US009060962B2

(12) United States Patent
Lodder et al.

(10) Patent No.: US 9,060,962 B2
(45) Date of Patent: Jun. 23, 2015

(54) D-TAGATOSE-BASED COMPOSITIONS AND METHODS FOR PREVENTING AND TREATING ATHEROSCLEROSIS, METABOLIC SYNDROME, AND SYMPTOMS THEREOF

(75) Inventors: Robert A. Lodder, Nicholasville, KY (US); Lisa A. Cassis, Nicholasville, KY (US)

(73) Assignee: UNIVERSITY OF KENTUCKY RESEARCH FOUNDATION, Lexington, KY (US)

(*) Notice: Subject to any disclaimer, the term of this patent is extended or adjusted under 35 U.S.C. 154(b) by 0 days.

(21) Appl. No.: 13/099,637

(22) Filed: May 3, 2011

(65) Prior Publication Data
US 2011/0263518 A1 Oct. 27, 2011

Related U.S. Application Data

(63) Continuation of application No. PCT/US2009/063293, filed on Nov. 4, 2009.

(60) Provisional application No. 61/193,192, filed on Nov. 4, 2008.

(51) Int. Cl.
*A61K 31/7034* (2006.01)
*A61K 31/7004* (2006.01)
*A61P 3/04* (2006.01)
*A61P 3/06* (2006.01)
*A61P 9/10* (2006.01)
*A61K 31/05* (2006.01)
*A61K 31/715* (2006.01)

(52) U.S. Cl.
CPC ............... *A61K 31/05* (2013.01); *A61K 31/715* (2013.01)

(58) Field of Classification Search
CPC .......................... A61K 31/715; A61K 31/05
USPC .............................................. 514/25, 731, 23
See application file for complete search history.

(56) References Cited

U.S. PATENT DOCUMENTS

| 3,536,809 A | 10/1970 | Applezweig |
| 3,598,123 A | 8/1971 | Zaffaroni |
| 3,845,770 A | 11/1974 | Higuchi et al. |
| 3,916,899 A | 11/1975 | Higuchi et al. |
| 4,008,719 A | 2/1977 | Higuchi et al. |
| 4,372,948 A | 2/1983 | Yoshikumi et al. |
| 4,786,722 A | 11/1988 | Zehner |
| 5,002,612 A | 3/1991 | Beadle et al. |
| 5,078,796 A | 1/1992 | Beadle et al. |
| 5,356,879 A | 10/1994 | Zehner et al. |
| 5,447,917 A | 9/1995 | Zehner et al. |
| 6,015,793 A | 1/2000 | Levin |
| 6,225,452 B1 | 5/2001 | Levin |
| 6,344,488 B1 | 2/2002 | Chenite et al. |
| 6,355,409 B1 | 3/2002 | Boelsterli |
| 6,432,464 B1 | 8/2002 | Andersen et al. |
| 6,592,906 B2 | 7/2003 | Neeser et al. |
| 6,989,171 B2 | 1/2006 | Portman |
| 6,991,923 B2 | 1/2006 | Bertelsen et al. |
| 7,163,961 B1 | 1/2007 | Yamori et al. |
| 7,189,351 B2 | 3/2007 | Levin et al. |
| 7,202,219 B1 | 4/2007 | Vigh et al. |
| 7,709,539 B2 * | 5/2010 | Chen et al. .................... 514/733 |
| 7,780,978 B2 | 8/2010 | Maurer et al. |
| 7,785,621 B2 | 8/2010 | Maurer et al. |
| 2001/0002269 A1 | 5/2001 | Zhao |
| 2001/0020008 A1 | 9/2001 | Levin |
| 2001/0033887 A1 | 10/2001 | Nesser et al. |
| 2002/0016300 A1 | 2/2002 | Meng et al. |
| 2002/0107222 A1 | 8/2002 | Platt |
| 2002/0137725 A1 | 9/2002 | Levin |
| 2002/0160090 A1 | 10/2002 | Lee et al. |
| 2002/0187232 A1 | 12/2002 | Lee et al. |
| 2002/0197352 A1 | 12/2002 | Portman |
| 2002/0197371 A1 | 12/2002 | Lee et al. |
| 2002/0197372 A1 | 12/2002 | Janssen et al. |
| 2003/0087834 A1 | 5/2003 | Levin |
| 2003/0099602 A1 | 5/2003 | Levin et al. |
| 2004/0028772 A1 | 2/2004 | Andersen |

(Continued)

FOREIGN PATENT DOCUMENTS

| EP | 0560284 | 9/1993 |
| JP | 6-65080 | 3/1994 |

(Continued)

OTHER PUBLICATIONS

Dunkley AJ, Charles K, et al. Effectiveness of interventions for reducing diabetes and cardiovascular disease risk in people with metabolic syndrome: systematic review and mixed treatment comparison meta-analysis. Diabetes Obs Metab 14:616-625, Jul. 2012.*

Buemann, B. et al., "D-Tagatose, a Stereoisomer of D-Fructose, Increases Hydrogen Production in Humans without Affecting 24-Hour Energy Expenditure or Respiratory Exchange Ratio," *Nature 128*, 1998, pp. 1481-1486.

Kim, S.H. et al., "Vitisin A inhibits adipocyte differentiation through cell cycle arrest in 3T3-L1 cells," *Biochem. Res. Commun. 372*, 2008, pp. 108-113.

Yanez, M. et al., "(−)—Trans-epsilon-viniferin, a polyphenol present in wines, is an inhibitor of noradrenaline and 5-hydroxytryptamine uptake and of monoamine oxidase activity," *Eur. J. Pharmacol.*, Aug. 7, 2006, 542(1-3):54-60.

(Continued)

*Primary Examiner* — Brandon Fetterolf
*Assistant Examiner* — Yih-Horng Shiao
(74) *Attorney, Agent, or Firm* — Pearl Cohen Zedek Latzer Baratz LLP

(57) ABSTRACT

Pharmaceutical compositions including D-tagatose along with a stilbene or stilbenoid component, or a salt or derivative thereof. Methods of prophylaxis and therapy by administering to a mammal a pharmaceutically effective amount of D-tagatose, optionally in combination with a stilbene or stilbenoid component, or a salt or derivative thereof to prevent or treat atherosclerosis, the metabolic syndrome, obesity, or diabetes.

13 Claims, No Drawings

(56) References Cited

U.S. PATENT DOCUMENTS

| | | |
|---|---|---|
| 2004/0037868 A1 | 2/2004 | Minich et al. |
| 2004/0082807 A1 | 4/2004 | Meng |
| 2004/0219280 A1 | 11/2004 | Green et al. |
| 2004/0220115 A1 | 11/2004 | Cham |
| 2005/0002880 A1 | 1/2005 | Mummert et al. |
| 2005/0032905 A1 | 2/2005 | Reo et al. |
| 2005/0048164 A1 | 3/2005 | Stahl |
| 2005/0106305 A1 | 5/2005 | Abraham et al. |
| 2005/0170041 A1 | 8/2005 | Abraham et al. |
| 2005/0203062 A1 | 9/2005 | Levin |
| 2005/0226960 A1 | 10/2005 | Boice et al. |
| 2005/0227928 A1 | 10/2005 | Carter et al. |
| 2005/0233459 A1 | 10/2005 | Melker et al. |
| 2005/0271707 A1 | 12/2005 | Maurer et al. |
| 2005/0282773 A1 | 12/2005 | Platt |
| 2006/0008508 A1 | 1/2006 | Maurer et al. |
| 2006/0024351 A1 | 2/2006 | Bradford |
| 2006/0034975 A1 | 2/2006 | Schechner et al. |
| 2006/0062734 A1 | 3/2006 | Melker et al. |
| 2006/0068072 A9 | 3/2006 | Lee et al. |
| 2006/0073255 A1 | 4/2006 | Catani et al. |
| 2006/0088637 A1 | 4/2006 | Goldman |
| 2006/0134294 A1 | 6/2006 | McKee et al. |
| 2006/0159801 A1 | 7/2006 | Rosenplenter et al. |
| 2006/0257344 A1 | 11/2006 | Nguyen et al. |
| 2006/0286202 A1 | 12/2006 | Boghani et al. |
| 2006/0286203 A1 | 12/2006 | Boghani et al. |
| 2006/0286259 A1 | 12/2006 | Hargreaves |
| 2007/0059418 A1 | 3/2007 | Catani et al. |
| 2007/0059419 A1 | 3/2007 | Catani et al. |
| 2007/0059421 A1 | 3/2007 | Catani et al. |
| 2007/0060639 A1 | 3/2007 | Wermeling |
| 2007/0082104 A1 | 4/2007 | De Baets |
| 2007/0110868 A1 | 5/2007 | Lee et al. |
| 2007/0116823 A1 | 5/2007 | Prakash et al. |
| 2007/0116828 A1 | 5/2007 | Prakash et al. |
| 2007/0160589 A1 | 7/2007 | Mattson |
| 2007/0212453 A1 | 9/2007 | Niness et al. |
| 2007/0259090 A1 | 11/2007 | Taylor et al. |
| 2007/0298502 A1 | 12/2007 | Eastwood et al. |
| 2008/0014331 A1 | 1/2008 | Badalov |
| 2008/0026111 A1 | 1/2008 | Bellody Jr. et al. |
| 2008/0031964 A1 | 2/2008 | Messadek |
| 2008/0059226 A1 | 3/2008 | Melker et al. |
| 2008/0069877 A1 | 3/2008 | Olsen et al. |
| 2008/0069933 A1 | 3/2008 | Ison et al. |
| 2008/0069934 A1 | 3/2008 | Ison et al. |
| 2008/0069935 A1 | 3/2008 | Ison et al. |
| 2008/0069936 A1 | 3/2008 | Ison et al. |
| 2008/0069937 A1 | 3/2008 | Ison et al. |
| 2008/0069938 A1 | 3/2008 | Ison et al. |
| 2008/0081093 A1 | 4/2008 | Ison et al. |
| 2008/0085354 A1 | 4/2008 | Paeschke et al. |
| 2008/0107775 A1 | 5/2008 | Prakash et al. |
| 2008/0107776 A1 | 5/2008 | Prakash et al. |
| 2008/0107787 A1 | 5/2008 | Prakash et al. |
| 2008/0152779 A1 | 6/2008 | De Groote et al. |
| 2008/0226776 A1 | 9/2008 | Roy et al. |
| 2008/0226788 A1 | 9/2008 | Chang et al. |
| 2008/0226789 A1 | 9/2008 | Roy et al. |
| 2008/0226790 A1 | 9/2008 | Johnson et al. |
| 2008/0226799 A1 | 9/2008 | Lee et al. |
| 2008/0260837 A1 | 10/2008 | Namburi et al. |
| 2008/0260899 A1 | 10/2008 | Schmidt et al. |
| 2008/0260925 A1 | 10/2008 | Zink |
| 2008/0292765 A1 | 11/2008 | Prakash et al. |
| 2008/0306093 A1 | 12/2008 | Servant et al. |
| 2009/0123638 A1 | 5/2009 | Eyal |
| 2009/0155363 A1 | 6/2009 | Maibach |
| 2009/0175997 A1 | 7/2009 | Ratnam et al. |
| 2009/0197837 A1 | 8/2009 | Desai et al. |
| 2009/0214729 A1 | 8/2009 | Shimek |
| 2009/0280232 A1 | 11/2009 | Lee et al. |
| 2009/0292010 A1 | 11/2009 | Shigemura et al. |
| 2009/0297634 A1 | 12/2009 | Friedman et al. |
| 2009/0299024 A1 | 12/2009 | Baceiredo et al. |
| 2009/0304759 A1 | 12/2009 | Howard, Jr. |
| 2010/0003370 A1 | 1/2010 | De Baets |
| 2010/0009038 A1 | 1/2010 | Ella et al. |
| 2010/0020008 A1 | 1/2010 | Kobayashi et al. |
| 2010/0041106 A1 | 2/2010 | Kim et al. |
| 2010/0112138 A1 | 5/2010 | Roy et al. |
| 2010/0130435 A1 | 5/2010 | Tokuda et al. |
| 2010/0166678 A1 | 7/2010 | Iida et al. |
| 2010/0233102 A1 | 9/2010 | Krammer et al. |

FOREIGN PATENT DOCUMENTS

| | | |
|---|---|---|
| JP | 2007527418 | 9/2007 |
| JP | 2009254242 | 11/2009 |
| JP | 2009286703 | 12/2009 |
| WO | WO 00/42865 | 7/2000 |
| WO | WO 02/058710 * | 8/2002 |
| WO | WO 03/059359 | 7/2003 |
| WO | WO 2006/079338 | 8/2006 |
| WO | WO 2007/032962 | 3/2007 |
| WO | WO 2007/073749 A1 | 7/2007 |
| WO | WO 2007/149865 A2 | 12/2007 |
| WO | WO 2008/059625 | 5/2008 |
| WO | WO 2008-59625 | 5/2008 |
| WO | WO 2008/071797 | 6/2008 |
| WO | WO 2009/080025 | 7/2009 |
| WO | WO 2009/080033 | 7/2009 |
| WO | WO 2009/137838 | 11/2009 |
| WO | WO 2010/014813 | 2/2010 |
| WO | WO 2010/054001 | 5/2010 |
| WO | WO 2010/075263 | 7/2010 |

OTHER PUBLICATIONS

Baur, J.A. et al., "Resveratrol improves health and survival of mice on a high calorie diet," *Nature,* 444(7117), Nov. 16, 2006, 337-42.

Jiang, W.J., "Sirtuins: novel targets for metabolic disease in drug development," *Biochem. Biophys. Res. Commun.,* 373(3), Aug. 29, 2008; 341-4.

Do, G.M. et al., Long-term effects of resveratrol supplementation on suppression of atherogenic lesion formation and cholesterol synthesis in apo E-deficient mice, *Biochem. Biophys. Res. Commun., 374(1),* Sep. 12, 2008; 374(1): 55-9.

Lærke et al. "D-Tagatose Has Low Small Intestinal Digestibility but High Large Intestinal Fermentability in Pigs[1,2,3]," *The Journal of Nutrition,* 129; 1002-1009 (1999).

Waffo-Teguo, P. et al., "Two New Stilbene Dirtier Glucosides from Grape(*vitis vinifers*) Cell Cultures," *Journal of Natural Products,* 64: 136-138 (2001).

Lu et al., "Tagatose, a New Antidiabetic and Obesity Control Drug," *Diabetes, Obesity and Metabolism,* 10: 109-134 (2008).

PCT/US2009/063293, International Search Report, Jun. 28, 2010, pp. 1-7.

PCT/US2009/063293, Written Opinion of the International Searching Authority, Jun. 28, 2010, pp. 1-6.

Levien et al., "New Drugs in Development for the Treatment of Diabetes," *Diabetes Spectrum,* 22(2): 92-106 (2009).

Espinosa et al., "Tagatose: from a Sweetener to a New Diabetic Medication?," *Expert Opin. Investig. Drugs,* 19(2): 285-294 (2010).

"Spherix Gets Promising Phase-3 Study Results of D-Tagatose in Type 2 Diabetes," Pharmabiz.com, Oct. 12, 2010.

PCT/US2011/28305, International Search Report, Jun. 16, 2011, pp. 1-4.

PCT/US2011/28305, Written Opinion of the International Searching Authority, Jun. 16, 2011, pp. 1-7.

Su, Hui-Chen et al., "Resveratrol, a Red Wine Antioxidant, Possesses an Insulin-like Effect in Streptozotocin-induced Diabetic Rats," Am. J. Physiol. Endocrinol. Metab. 2006, vol. 290, No. 6, p. E1339-E1346.

Pezet, Roger et al., "δ-Viniferin, a Resveratrol Dehydrodimer: One of the Major Stilbenes Synthesized by Stressed Grapevine Leaves," J. Agric. Food. Chem., 2003, vol. 51, No. 18, p. 5488-5492.

Egger, Swinburn, "An "ecological" Approach to the Obesity Pandemic," BMJ. 1997, vol. 315, p. 477-480.

(56) References Cited

OTHER PUBLICATIONS

Rocchini, "Obesity Hypertension," Am. J. Hypertens. 2002, vol. 15, No. 2.2, p. S50-S52.
Despres, Lemieux, "Abdominal Obesity and Metabolic Syndrome," Nature. 2006, vol. 444, p. 881-887.
Grundy, Brewer et al., "Definition of Metabolic Syndrome: Report of the National Heart, Lung, and Blood Institute/ American Heart Association Conference on Scientific Issues Related to Definition," Arterioscler. Thromb. Vasc. Biol. 2004, vol. 24, p. e13-e18.
Serdula, Mokdad et al, "Prevalence of Attempting Weight Loss and Strategies for Controlling Weight," JAMA. 1999, vol. 282, p. 1353-1358.
Levin, "Tagatose, the New GRAS Sweetener and Health Product," J. Med. Food. 2002, vol. 5, p. 23-36.
Rulis AM. Agency Response Letter GRAS Notice nr GRN 000078. US Food [Q2J and Drug Administration: <http://www.cfsan.fda.gov/-rdb/opa-g078.html>.
Storlien, Oaks et al., "Syndromes of Insulin Resistance in the Rat. Inducement by Diet and Amelioration with Benfluorex," Diabetes. 1993, vol. 42, p. 457-462.
Martinez, Rizza et al., "High-Fructose Feeding Elicits Insulin Resistance, Hyperinsulinism, and Hypertension in Normal Mongrel Dogs," Hypertension. 1994, vol. 23, p. 456-463.
Srinivasan, Clevidence et al., "Varied Effects of Dietary Sucrose and Cholesterol on Serum Lipids, Lipoproteins and Apolipoproteins in Rhesus Monkeys," Atherosclerosis. 1979, vol. 33, p. 301-314.
Swanson, Laine et al., "Metabolic Effects of Dietary Fructose in Healthy Subjects," Am. J. Clin. Nutr. 1992, vol. 55, p. 851-856.
Merkel, Velez-Carrasco et al., "Compared with Saturated Fatty Acids, Dietary Monounsaturated Fatty Acids and Carbohydrates Increase Atherosclerosis and VLDL Cholesterol Levels in LDL Receptor-Deficient, But Not Apolipoprotein E-Deficient , Mice," Proc. Natl. Acad. Sci. USA. 2001, vol. 98, p. 13294-13299.
Gregorevic, Allen et al., "rAAV6-microdystrophin Preserves Muscle Function and Extends Lifespan in Severely Dystrophic Mice," Nat. Med. 2006, vol. 12, p. 787-789.
Henriques, Huang et al., "Orchidectomy, But Not Ovarlectomy, Regulates Angiotensin II-Induced Vascular Diseases in Apolipoprotein E-Deficient Mice," Endocrinology. 2004, vol. 145, p. 3866-3872.
Jawien, Nastalek et al., "Mouse Models of Experimental Atherosclerosis," J. Physical. Pharmacol. 2004, vol. 55, p. 503-517.
Buemann, Toubro et al., "The Acute Effect of D-Tagatose on Food Intake in Human Subjects," Br. J. Nutr. 2000, vol. 84, p. 227-231.
Rada, Avena et al., "Daily Bingeing on Sugar Repeatedly Releases Dopamine in the Accumbens Shell," Neuroscience. 2005, vol. 134, p. 737-744.
Donner, Wilber et al., "D-Tagatose, A Novel Hexose: Acute Effects on Carbohydrate Tolerance in Subjects With and Without Type 2 Diabetes," Diabetes Obes. Metab. 1999, vol. 1, p. 285-291.
Donner, "The Metabolic Effects of Dietary Supplementation With D-Tagatose in Patients With Type 2 Diabetes," Diabetes. 2006, 55(Suppl1):A110; 461P.
Rognstad, "Gluconeogenesis From D-Tagatose by Isolated Rat and Hamster Liver Cells," FEBS Lett. 1975, vol. 52, p. 292-294.
Seoane, Gomez-Foix et al., "Glucose 6-Phosphate Produced by Glucokinase, But Not Hexokinase I, Promotes the Activation of Hepatic Glycogen Synthase," J. Biol. Chem. 1996, vol. 271, p. 23756-23760.
Gergely, Toth et al., "Effect of Fructose 1-Phosphate on the Activation of Liver Glycogen Synthase," Biochem. J. 1985, vol. 232, p. 133-137.
Weisberg, McCann et al., "Obesity is Associated With Macrophage Accumulation in Adipose Tissue," J. Clin. Invest. 2003, vol. 112, p. 1796-1808.
Skurk, Alberti-Huber et al., "Relationship Between Adipocyte Size and Adipokine Expression and Secretion," J. Clin. Endocrinol. Metab. 2007, vol. 92, p. 1023-1033.
Xu, Barnes et al., "Chronic Inflammation in Fat Plays a Crucial Role in the Development of Obesity-Related Insulin Resistance," J. Clin. Invest. 2003, vol. 112, p. 1821-1830.
Libby, "Current Concepts of the Pathogenesis of the Acute Coronary Syndromes," Circulation. 2001, vol. 104, p. 365-372.
Cullen, Baetta et al., "Rupture of the Atherosclerotic Plaque: Does a Good Animal Model Exist?," Arlerioscler. Thromb. Vasc. Biol. 2003, vol. 23, p. 535-542.
Saunders, Zehner et al., "Disposition of D-[U-14C]tagatose in the rat," Regul. Toxicol. Pharmacol. 1999, vol. 29(2pt2), p. S46-S56.
Torpy, J.M. et al., "The Metabolic Syndrome," JAMA. 2006, vol. 295, No. 7, p. 850.
Metts, Thatcher et al., "DDDAS Design of Drug Interventions for the Treatment of Dyslipidemia in ApoE$^{-/-}$Mice," J Develop Drugs. 2013, vol. 2, Issue.2.
Assalit, Billard et al., "2,20-Bipyridine-3,30-dicarboxylic carbohydrate esters and amides. Synthesis and preliminary evaluation as ligands in Cu(II)-catalysed enantioselective electrophilic fluorination," Tetrahedron: Asymmetry. 2009, vol. 20, p. 593-601.
European Search Report issued for European Patent Application No. 09825367.7 dated Apr. 2, 2012.
Larkin, Ta et al., "Dietary combination of soy with a probiotic or prebiotic food significantly reduces total and LDL cholesterol in mildly hypercholesterolaemic subjects," Eur. J. Clin. Nutr. 2009, vol. 63, Issue. 2, p. 238-245.
Penumathsa, Suresh V. et al., "Statin and Resveratrol in Combination induces Cardioprotection against Myocardial Infarction in Hypercholesterolemic Rat," J. Mol. Cell. Cardiol. 2007, vol. 42, Issue. 3, p. 508-516.
Park, Ock J. et al., "Resistant Starch Supplementation Influences Blood Lipid Concentrations and Glucose Control in Overweight Subjects," J. Nutr. Sci. Vitaminol. 2004, vol. 50, Issue 2, p. 93-99.
Lopez, Hubert W. et al., "Class 2 Resistant Starches Lower Plasma and Liver Lipids and Improve Mineral Retention in Rats," J. Nutr. 2001, vol. 131, Issue. 4, p. 1283-1289.
Younes, H. et al., "Resistant starch is more effective than cholestyramine as a lipid-lowering agent in the rat," Lipids. 1995, vol. 30, Issue. 9, p. 847-853.
Xing, Wei-Wei et al., "Effects of polydatin from Polygonum cuspidatum on lipid profile in hyperlipidemic rabbits," Biomed. Pharmacother., 2009, vol. 63, Issue. 7, p. 457-462.

* cited by examiner

D-TAGATOSE-BASED COMPOSITIONS AND METHODS FOR PREVENTING AND TREATING ATHEROSCLEROSIS, METABOLIC SYNDROME, AND SYMPTOMS THEREOF

CROSS REFERENCE TO RELATED APPLICATIONS

This is a continuation application of Application No. PCT/US2009/063293 filed Nov. 4, 2009, which claims priority to U.S. Provisional Application No. 61/193,192 filed on Nov. 4, 2008, the contents of each which is hereby incorporated herein in its entirety by express reference thereto.

TECHNICAL FIELD

The present invention relates generally to pharmaceutical compositions including a pharmaceutically effective amount of D-tagatose in combination with a pharmaceutically acceptable amount of a stilbene or stilbenoid component, or a salt or derivative thereof; or a combination thereof. Also included are methods for the prevention or treatment of atherosclerosis, the metabolic syndrome, obesity, and diabetes by administering a pharmaceutically effective amount of D-Tagatose, or a salt or derivative thereof, or any of the above-noted compositions, to a mammal. The invention further relates to stable food and pharmaceutical products including such compositions.

BACKGROUND OF THE INVENTION

D-tagatose (TAG), also known as (3S,4S,5R)-1,3,4,5,6-pentahydroxy-hexan-2-one or Naturlose®, is a ketohexose, isomer of fructose and functional sweetener. It is a white anhydrous crystalline solid and has a molecular weight of 180.16 and empirical formula of $C_6H_{12}O_6$. It is about 92% as sweet as sucrose and has been reported for use as a nutritive or low-calorie sweetener. Only about 25% of TAG ingested in humans is absorbed into the bloodstream. TAG is a naturally occurring molecule found in heated dairy products, including sterilized and powdered cow's milk, hot cocoa, various cheeses and yogurt, although TAG can also be chemically manufactured. Various patents disclose information regarding TAG and its conventional uses.

U.S. Pat. No. 6,991,923 discloses a process for manufacturing TAG that includes hydrolyzing lactose to galactose and glucose, isomerizing galactose to tagatose and then chromatographically separating the compounds and recycling any unconverted compounds. TAG supplies 1.5 kcal/g of energy (as compared to 4 kcal/g from sucrose), in large part because TAG is incompletely absorbed by the small intestine. Some uses of TAG include as a sweetener in diet beverages at concentrations up to 1%, light ice creams or yogurts at concentrations up to 3%, and regular or dietetic hard candies at levels up to 15%.

U.S. Pat. No. 4,786,722 discloses a process for the preparation of a sweetened edible formulation in which the sweetening agent is less caloric than sucrose which includes the step of mixing a foodstuff with an amount sufficient to sweeten the foodstuff with TAG.

U.S. Pat. No. 5,356,879 discloses a method for preventing the formation of advanced glycosylation end-products in a mammal including administering to said mammal an effective amount of TAG.

U.S. Pat. No. 5,447,917 discloses TAG as an anti-hyperglycemic agent.

U.S. Pat. No. 7,202,219 teaches a method for selectively inducing production of butyrate by bacteria in the colon of a human in need thereof by administering TAG. Butyrate is reported to allegedly have a colon cancer protective effect.

Stilbenes and stilbenoids are diarylethenes, stilbenoids being hydroxylated derivatives of stilbenes. Stilbenes and stilbenoids can be found naturally in berries and in the heart wood of the Indian Kino tree, a known medicinal plant in India. Stilbenes have the basic empirical formula of $C_{14}H_{12}$. A common stilbenoid is resveratrol, also known as 3,5,4'-trihydroxystilbene, a natural component found in the skin of red grapes. Resveratrol is an off-white powdery substance when extracted with methanol and has a molecular weight of 228.24 and an empirical formula of $C_{14}H_{12}O_3$. Resveratrol has been reported to improve health and longevity of mice on high calorie diets under certain circumstances (Baur, J. A., et al., "Resveratrol improves health and survival of mice on high-calorie diet," *Nature*, 444(7117):337-42 (2006)). Pterostilbene, also known as 3,5-dimethoxy-4'-hydroxystilbene, is chemically related to resveratrol and may possess many similar properties. Pterostilbene is a white or off-white crystal powder and has a molecular weight of 256 and an empirical formula of $C_{16}H_{16}O_3$.

Diabetes, sometimes known as diabetes mellitus, is a group of disorders characterized by an insufficient amount of, or failure to respond properly to, insulin. There are many forms of diabetes including: Type 1, which results from a failure to produce insulin; and Type 2 which results from insulin resistance; gestational diabetes which occurs in pregnant women who have high glucose levels; and various other types including congenital diabetes, steroid diabetes and monogenic diabetes. As a result of the insulin deficiencies, diabetics typically have hyperglycemia and are subject to acute and chronic complications such as ketoacidosis, and nonketotic hyperosmolar coma. Long-term complications include cardiovascular disease, chronic renal failure, retinal damage, nerve damage, microvascular damage and poor circulation and wound healing. Treatment options currently include the use of insulin, diabetic and blood pressure medications, as well as diet and exercise. Blood glucose monitoring is usually an essential part of treatment as hypoglycemia, or abnormally low blood glucose, can occur as a result of diabetes treatment and/or medications. ("Diabetes Overview," *Nat'l Institute of Diabetes and Digestive and Kidney Diseases, NIH*, (2006)).

Atherosclerosis is a syndrome in which the walls of arterial blood vessels are thickened, usually as a result of a build-up of fatty materials such as cholesterol. This syndrome can be promoted by the presence of a high amount of low density lipoproteins ("LDLs") as well as a low amount of high density lipoproteins ("HDLs") and a high serum triglyceride concentration. Atherosclerotic patients typically have plaques containing macrophage cells that have taken up oxidized LDLs, lipids such as cholesterol and fatty acids, calcium and fibrous connective tissue that build up along artery walls. Over time, narrowing or complete closure of arteries can result, decreasing the amount of blood supply to the organs and tissues the arteries feed. Additionally, an aneurysm may occur as a result of the artery enlarging to compensate for the blockage. This leads to an increased risk of rupture, which can result in a severe hemorrhage. Alternatively, the plaque may rupture and cause the formation of a thrombus, which can rapidly decrease blood flow to an area. Risk factors include having high blood pressure, diabetes, dyslipoproteinemia, smoking, and high C-reactive protein concentrations in the blood. Treatment options include the medicinal intake of statins, niacin, aspirin and cholesterol-lowering drugs as well as lifestyle modifications such as diet and exercise. Sometimes angioplasty is performed where stents may be inserted to expand narrowed arteries. ("Atherosclerosis," *American Heart Association*, available at: http://www.americanheart.org/print_presenter.jhtml:jsessionid=FCG5JBCHQDELMCQFCXPSCZQ?identifier=4440 (2009)).

The Centers for Disease Control (CDC) reports that about two-thirds of the adult population in the United States is classified as either overweight or obese, as defined by a body mass index ("BMI") of >25 kg/m$^2$ or >30 kg/m$^2$, respectively. Obesity and weight gain reportedly have many causes including overeating, genetics, psychological factors, lifestyle, sex, age, medications, distribution of body fat and certain medical conditions including hyperthyroidism, Cushing syndrome, polycystic ovarian syndrome, and Prader-Willi syndrome. Obesity has been reported to increase the likelihood of various diseases and health problems including heart disease, type 2 diabetes, hypertension, stroke, certain types of cancer including breast and colon, gallstones, gout, depression, sleep apnea and osteoarthritis. Treatment reportedly includes dieting, physical exercise, behavior modification and sometimes anti-obesity drugs such as appetite suppressants, and surgery such as malabsorptive procedures and restrictive procedures. Obesity is the second leading cause of preventable deaths in the United States. ("Overweight and Obesity," *Centers for Disease Control and Prevention*, available at: http://www.cdc.gov/obesity/index.html, (2009)).

The metabolic syndrome is characterized by a group of factors and lab test results, which have been alleged to include obesity, weight gain, atherogenic dyslipidemia, especially lower than normal levels of high-density lipoprotein (HDL) cholesterol, hypertension, high serum triglyceride levels (≥150 mg/dl), hypertension, insulin resistance or glucose intolerance and a proinflammatory state characterized by elevated C-reactive protein in the blood. (Torpy, J. M., et al., "The Metabolic Syndrome," *JAMA*, 295(7): 850 (2006)). Genetic predispositions to these risk factors increase the likelihood of developing the metabolic syndrome. People with the metabolic syndrome are reportedly at an increased risk of type 2 diabetes, lipodystrophy and cardiovascular disease, such as coronary heart disease, stroke, and peripheral vascular disease. Typically patients with the metabolic syndrome are overweight or obese. Some environmental factors are reported to contribute to the development of the syndrome, such as a sedentary life-style, smoking, and a high carbohydrate diet. Metabolic syndrome is also sometimes associated with liver and kidney problems as well as polycystic ovary syndrome and cognitive decline in the elderly. Reported treatment can consist of lifestyle changes including diet and exercise, as well as medication to treat the disease and the symptoms individually.

It is desired to have compositions and methods to prevent or treat the metabolic syndrome and its underlying causes, as well as atherosclerosis, obesity, and diabetes.

SUMMARY OF THE INVENTION

The invention encompasses compositions, as well as methods of employing them that may advantageously improve the prevention or treatment, or both, of the metabolic syndrome, atherosclerosis, obesity and diabetes, or any combination thereof.

In one embodiment, the pharmaceutical composition includes a pharmaceutically effective amount of D-tagatose, or a pharmaceutically acceptable salt, sugar alcohol, hydrate, solvate, ester, amide, derivative, analog, metabolite, prodrug thereof, and a pharmaceutically effective amount of at least a second pharmaceutically active drug (also referred to herein as a "second active drug component"). In preferred embodiments, the second pharmaceutically active drug component includes a stilbene or stilbenoid component, or any pharmaceutically acceptable salt, alcohol, hydrate, ester, amide, derivative, analog, polymorph, metabolite, isomer, or prodrug form thereof, or any combination thereof.

Preferred stilbene or stilbenoid components may include resveratrol or a resveratrol derivative, or a combination thereof. A preferred resveratrol derivative includes one or more resveratrol dimers. Preferred resveratrol dimers include resveratrol trans-dehydrodimer, resveratrol (E)-dehydrodimer 11'-O-β-D-glucopyranoside, resveratrol (E)-dehydrodimer 11-O-β-D-glucopyranoside and viniferins, or an isomer thereof, or any combination thereof.

In another embodiment, the pharmaceutical composition is an anti-metabolic syndrome composition that includes any of the compositions herein where the pharmaceutically effective amount of the composition is sufficient to prevent or treat the metabolic syndrome. In this embodiment, the second active drug component is present in an amount sufficient to prevent or treat the metabolic syndrome, particularly in combination with the D-tagatose.

Alternatively, the pharmaceutical composition may be an anti-atherosclerosis composition that includes any of the compositions herein where the pharmaceutically effective amount of the composition is sufficient to prevent or treat the atherosclerosis syndrome. In this embodiment, the second active drug component is present in an amount sufficient to prevent or treat atherosclerosis, particularly in combination with the D-tagatose.

Alternatively, the pharmaceutical composition may be an anti-obesity composition that includes any of the compositions herein where the pharmaceutically effective amount of the composition is sufficient to prevent or treat obesity. In this embodiment, the second active drug component is present in an amount sufficient to prevent or treat the metabolic syndrome, particularly in combination with the D-tagatose.

Alternatively, the pharmaceutical composition may be an anti-diabetes composition that includes any of the compositions herein where the pharmaceutically effective amount of the composition is sufficient to prevent or treat diabetes. In this embodiment, the second active drug component is present in an amount sufficient to prevent or treat diabetes, particularly in combination with the D-tagatose.

In one embodiment, the pharmaceutical composition, including D-tagatose or any of the pharmaceutical compositions described herein, are present in an amount sufficient enough to decrease the total serum triglyceride levels by about 1% to about 60%, preferably about 5% to about 50%, more preferably about 11% to about 40%.

In another embodiment, the pharmaceutical compositions, including D-tagatose or any of the pharmaceutical compositions described herein, are present in an amount sufficient enough to decrease the concentration of low-density lipoprotein (LDL) in blood by about 0.1% to about 30%, preferably about 4% to about 20%, more preferably about 6% to about 10%.

In one embodiment, the pharmaceutical compositions, including D-tagatose or any of the pharmaceutical compositions described herein, are present in an amount sufficient enough to decrease the plaque volume in arteries by about 0.1% to about 50%, preferably about 0.5% to about 40%, more preferably about 1% to about 30%.

The invention also encompasses methods for preventing or treating the metabolic syndrome in a mammal, which includes administering to the mammal a pharmaceutically effective amount of a composition including D-tagatose or any of the pharmaceutical compositions discussed herein (e.g., a combination of D-tagatose and a stilbene or stilbenoid component), to prevent or treat the metabolic syndrome in the mammal. Preferably, the mammal is a human. In some embodiments, the pharmaceutical composition is adapted for oral administration and the methods include administering the pharmaceutical composition orally.

The invention further encompasses a method for preventing or treating atherosclerosis in a mammal, which includes administering to the mammal a pharmaceutically effective amount of a composition including any of the compositions described herein (e.g., a combination of D-tagatose and a stilbene or stilbenoid component) to prevent or treat the atherosclerosis in the mammal. Preferably, the mammal is a human. In one preferred embodiment, the pharmaceutical composition is adapted for oral administration and the methods including orally administering the compositions. As used in the methods, the compositions typically may include D-tagatose, D-tagatose and a stilbene or stilbenoid component, or any combination thereof, in any of the forms described herein.

In another embodiment, the invention includes methods for preventing or treating obesity in a mammal, which includes administering to the mammal a pharmaceutically effective amount of a composition, including D-tagatose or any of the pharmaceutical compositions described herein, to prevent or treat obesity in the mammal.

In another embodiment, the invention includes methods for preventing or treating diabetes in a mammal, which includes administering to the mammal a pharmaceutically effective amount of a composition, including D-tagatose or any of the pharmaceutical compositions described herein, to prevent or treat diabetes in the mammal.

In one embodiment, the pharmaceutical compositions may be adapted for oral or nasal administration. In a preferred embodiment, the compositions are adapted for oral administration and formed as a tablet. In an exemplary embodiment, the tablet may be formed by direct compression.

In other embodiments, any of the pharmaceutical compositions herein are used in the prevention or treatment of the metabolic syndrome; in the prevention or treatment of atherosclerosis; in the prevention or treatment of obesity; or in the prevention or treatment of diabetes; or a combination thereof.

In another embodiment, the pharmaceutical compositions are for use as a medicament. In various embodiments, the pharmaceutical compositions are for use as a medicament for preventing or treating the metabolic syndrome; as a medicament for preventing or treating atherosclerosis; as a medicament for preventing or treating obesity; or as a medicament for preventing or treating diabetes; or a combination thereof.

In various embodiments, the invention encompasses the use of any of the pharmaceutical compositions mentioned herein in the manufacture of a medicament for the prevention or treatment of one or more symptoms of the metabolic syndrome; in the manufacture of a medicament for the treatment or ameliorating one or more symptoms of atherosclerosis; in the manufacture of a medicament for the treatment or ameliorating one or more symptoms of obesity; in the manufacture of a medicament for the treatment or ameliorating one or more symptoms of diabetes; or a combination thereof.

In an exemplary embodiment, the use of a pharmaceutically effective amount of the pharmaceutical compositions herein is in the manufacture of a medicament for the prevention or treatment of one or more symptoms of hypertension, hypertriglyceridemia, hyperglycemia, hypercholesterolemia, or a combination thereof. In the case of diabetes, a preferred embodiment is the use of a pharmaceutically effective amount of a composition discussed herein to prepare a medicament for the prevention or treatment of hyperglycemia symptom(s).

In another embodiment, the invention encompasses the use of any or all of the pharmaceutical compositions herein in therapy. In another embodiment, the invention encompasses the use of any or all of the pharmaceutical compositions herein for prophylaxis.

In a preferred embodiment, the pharmaceutical composition includes a pharmaceutically effective amount of D-tagatose, or a pharmaceutically acceptable salt, sugar alcohol, hydrate, solvate, ester, amide, derivative, analog, metabolite, prodrug thereof, and a second pharmaceutically active drug component that includes a stilbene or stilbenoid component, or any pharmaceutically acceptable salt, alcohol, hydrate, ester, amide, derivative, analog, polymorph, metabolite, isomer, or prodrug thereof, or any combination thereof, that is used in the therapy, prevention or treatment of a human that has, is suspected of having, or at risk for developing the metabolic syndrome.

In another preferred embodiment, the pharmaceutical composition includes the same composition as in the preceding paragraph and is used in the therapy, prevention or treatment of a human that has, is suspected of having, or at risk for developing atherosclerosis.

In another preferred embodiment, the pharmaceutical composition includes the same composition as in the preceding paragraphs and is used in the therapy, prevention or treatment of a human that has, is suspected of having, or at risk for developing obesity.

In another preferred embodiment, the pharmaceutical composition includes the same composition as in the preceding paragraphs and is used in the therapy, prevention or treatment of a human that has, is suspected of having, or at risk for developing diabetes.

The invention also encompasses food products that include a pharmaceutically effective amount of D-tagatose, or a pharmaceutically acceptable salt, sugar alcohol, hydrate, solvate, ester, amide, derivative, analog, metabolite, prodrug thereof, and a pharmaceutically effective amount of a second active ingredient component described herein. The second active ingredient component includes a stilbene or stilbenoid component as discussed herein.

In the practice of any of the methods of the invention, the composition administered to the mammal may also further optionally include the second active drug component. In a preferred embodiment, the food product includes an effective amount of a stilbene or stilbenoid component, or any pharmaceutically acceptable salt, alcohol, hydrate, ester, amide, derivative, analog, polymorph, metabolite, isomer, or prodrug thereof, or any combination thereof. A preferred stilbene or stilbenoid component includes one or more of resveratrol or a resveratrol derivative, or a combination thereof. A preferred resveratrol derivative includes a resveratrol dimer. Preferred resveratrol dimers include resveratrol trans-dehydrodimer, resveratrol (E)-dehydrodimer 11'-O-β-D-glucopyranoside, resveratrol (E)-dehydrodimer 11-O-β-D-glucopyranoside and viniferins, or an isomer thereof, or a combination thereof.

While the practice of the invention is contemplated to have the most relevant and most immediate utility in the prevention and treatment of the metabolic syndrome, atherosclerosis, obesity and diabetes, the scope of the present disclosure is not intended to be interpreted as being limited only to the administration of a specific composition as enumerated herein.

Indeed, without being bound by theory, it is believed that the compositions and methods herein may find broad applicability in a variety of treatment/prophylaxis regimens, including other diseases and syndromes. It should also be understood that each of the embodiments described herein may typically be used in connection with any of the other embodiments described herein.

DETAILED DESCRIPTION OF PREFERRED EMBODIMENTS

It has now been discovered that pharmaceutically effective compositions including a pharmaceutically effective amount of D-tagatose, or a pharmaceutically acceptable salt, sugar alcohol, hydrate, solvate, ester, amide, derivative, analog, metabolite, prodrug thereof; alone or preferably in combination with a pharmaceutically effective amount of at least a second pharmaceutically active drug, or a pharmaceutically acceptable salt, alcohol, hydrate, ester, amide, derivative, analog, polymorph, metabolite, isomer, or prodrug thereof, have surprising and unexpected prophylactic or therapeutic effect in mammals, preferably humans. Preferably, the compositions involve a combination of pharmaceutically effective amounts of D-tagatose and at least a second pharmaceutically active drug, and may also contain a pharmaceutically acceptable carrier, and optionally, one or more additional prophylactic or therapeutic ingredients. Methods for preventing or treating metabolic syndrome, atherosclerosis, obesity, or diabetes by administering a prophylactically or therapeutically effective amount of the above-noted pharmaceutical compositions with respect to each such indication have also been discovered. Preferably, the second pharmaceutically active drug includes a stilbene or stilbenoid component, or any pharmaceutically acceptable salt, alcohol, hydrate, ester, amide, derivative, analog, polymorph, metabolite, isomer, or prodrug form thereof; or any combination thereof.

An active pharmaceutical ingredient in the present compositions and methods is D-tagatose ("TAG"). Although TAG can be used in any state, including as a salt, sugar alcohol, hydrate, solvate, ester, amide, derivative, analog, metabolite thereof, it is preferably included as an active ingredient in its natural state, i.e., not in the form of a salt, sugar alcohol, hydrate, solvate, ester, amide, derivative, analog, or metabolite. As used herein, "TAG" includes the active agent itself, or an active metabolite, pharmaceutically acceptable salt, sugar alcohol, hydrate, solvate, ester, amide, derivative, analog, metabolite, prodrug or any combination thereof. "TAG" also includes polymorphs of the active ingredient. "Salt" and the other forms noted herein in connection with TAG and any other pharmaceutically active drug component herein refers to pharmaceutically acceptable forms in pharmaceutical compositions and food products. These same forms may be included in the compositions and methods with reference to the second pharmaceutically active drug for any of the pharmaceutically active ingredients discussed herein, as well.

In another embodiment, the present invention relates to a pharmaceutical composition including pharmaceutically effective amounts of a first active drug, namely TAG, in combination with at least a second pharmaceutically active drug. The second active drug component may be any drug, metabolite, or prodrug pharmaceutically useful in combination therapy with the first active drug TAG.

In one preferred embodiment, the second active drug component preferably includes or is a stilbene or stilbenoid component (i.e., one or more stilbenes, stilbenoids, or a combination thereof) in any form, including but not limited to any pharmaceutically acceptable salt, alcohol, hydrate, ester, amide, derivative, analog, polymorph, metabolite, isomer, or prodrug form, or any combination thereof. Thus, the term "stilbene or stilbenoid component" means one or more stilbene, one or more stilbenoid, or any combination thereof in any of the forms noted herein. These stilbene and stilbenoid compounds may be obtained by any suitable technique available to those of ordinary skill in the art, including but not limited to chemical synthesis or by extraction and optional isolation or purification from a plant. The stilbene compounds can be formed into pharmaceutically acceptable acid-addition salts and salts with bases. The stilbene and stilbenoid component preferably includes one or more of: piceatannol, pinosylvin, pterostilbene, resveratrol, viniferins, ampelopsin A, ampelopsin E, diptoindonesin C, diptoindonesin F, gnetin H, hemsleyanol D, hopeaphenol, trans-diptoindonesin B, vaticanol B, astringin, piceids, and diptoindonesin A, or any combination thereof.

A preferred stilbenoid included in the second active drug component may be one or more of resveratrol and derivative(s) thereof. Resveratrol can be synthesized via the phenylalanine/polymalonate pathway in plants and is found in the skin of red grapes. Resveratrol is a fat-soluble compound that occurs in both cis- and trans-configurations, each of which can form one or more glucosides. Resveratrol may also be obtained by chemical isolation from plant-derived compositions or synthesized. It has been reported that about 70% of resveratrol dosed orally is absorbed by the human body. Due to its rapid metabolism by the small intestine and liver, which lowers its bio-availability, higher doses of resveratrol may be preferred. The second active drug component preferably includes one or more resveratrol-derived components, including, but not limited to one or more resveratrol dimers, more preferably resveratrol trans-dehydrodimer, resveratrol (E)-dehydrodimer 11'-O-β-D-glucopyranoside, resveratrol (E)-dehydrodimer 11-O-β-D-glucopyranoside and viniferins, or isomers thereof, or any combination thereof.

Resveratrol trans-dehydrodimer, also known as resveratrol (E)-dehydrodimer, is heterocyclic, has an empirical formula of $C_{28}H_{22}O_6$ and a molecular weight of 454.48. Resveratrol (E)-dehydrodimer 11'-O-β-D-glucopyranoside, also known as (2S,3R,4S,5S,6R)-2-(3-{(E)-2-[(2S,3S)-3-(3,5-Dihydroxy-phenyl)-2-(4-hydroxy-phenyl)-2,3-dihydro-benzofuran-5-yl]-vinyl}-5-hydroxy-phenoxy)-6-hydroxymethyl-tetrahydropyran-3,4,5-triol, is heterocyclic, has an empirical formula of $C_{34}H_{32}O_{11}$ and a molecular weight of 616.62.

Viniferins are glycosylated and polymerized derivatives of resveratrol. A preferred component of the second active ingredient is epsilon viniferin (ε-viniferin), which is a cyclic dimer of resveratrol and can be extracted from *Vitis vinifera*. This compound is typically formed through the peroxidase-mediated oxidative dimerization of resveratrol. ε-viniferin, also known as 5-{6-hydroxy-2-(4-hydroxyphenyl)-4-[2-(4-hydroxyphenyl)vinyl]-2,3-dihydroxybenzofuran-3-yl}benzene-1,3-diol, is heterocyclic and has an empirical formula of $C_{28}H_{22}O_6$ and a molecular weight of 454.48.

The stilbenoid of the second active drug component may preferably include one or more piceids. Resveratrol can conjugate to sugars, which can form one or more glucosides such as trans- and cis-piceid, the 3-O-β-D-resveratrol glucoside. A preferred second active drug component includes trans-(14C6)piceid. Trans-(14C6)piceid is heterocyclic, has an empirical formula of $C_{20}H_{22}O_8$ and a molecular weight of 402.32.

The magnitude of a prophylactic or therapeutic dose of the compositions of the invention in the acute or chronic management of disease will vary depending on the subject to which it is being administered, the severity of the condition to be treated, and the route and manner of administration, and may be determined by one of ordinary skill in the art with reference to the guidance provided herein. The dose, and perhaps the dose frequency, will also vary according to the age, body weight, and response of the individual patient based on the guidance herein. In general, the total daily dose range, for the conditions described herein, is from about 0.01 grams to about 240 grams, preferably about 0.1 grams to 200 grams, and more preferably about 0.5 grams to 100 grams of TAG. In exemplary embodiments, the pharmaceutically effective amount of TAG may include about 0.75 grams to 90 grams, about 1 gram to 80 grams, or even about 1.5 grams to 75 grams, or any whole number therebetween. In a preferred embodiment, the pharmaceutically effective amount of TAG is about 2 grams, about 2.5 grams, about 5 grams, about 7.5 grams, about 15 grams, about 25 grams, or about 50 grams. In general, the total daily dose range for the conditions described herein is about 0.0001 grams to about 1.5 grams, preferably about 0.001 grams to about 0.75 grams, and more preferably about 0.005 grams to about 0.5 grams of the stilbene or stilbenoid component. An exemplary amount of stilbene or stilbenoid component is about 0.01 grams to about 0.1 grams.

The compositions can be administered in single or divided doses, preferably with the total daily dose divided into equal dosages taken over the course of a day. Preferably, only one dose per day will be required. In one embodiment, the composition that is administered will be taken with food and drink (e.g., within about 2 hours of eating, preferably within about one hour of eating) so as to eliminate any potential gastrointestinal distress. In another embodiment, the compositions may be administered without regard to eating, while in another the compositions will be included in a food product and administered as a food product.

The pharmaceutically effective compositions discussed herein, including TAG and optionally a second active drug component, which may independently be prophylactic, therapeutic, or help manage, e.g., the condition or disease or its symptoms, may be administered in any dosage form(s) suitable to administer a measured amount of the pharmaceutical composition to achieve the desired prophylactic or therapeutic effect based at least on the guidance herein. Such dosage forms include, for example, solid dosage forms, such as tablets, capsules, powders, and cachets, or liquid dosage forms, such as suspensions, syrups, solutions, and elixirs. The second drug component may be combined with the TAG composition or may be administered in a separate dosage form, but preferably is in tablet form. The dosage form containing the second active drug component will, in any event, contain a quantity of the additional active drug(s) in an amount effective to alleviate or manage the symptoms or condition of the subject being treated or to provide a prophylactic effect. The selection of the specific second active drug component will depend upon the specific disease state being treated, some of which are described in detail herein. Preferably, all active ingredients will be in an oral form, e.g., an oral composition or tablet, capsule, powder, and/or cachets, more preferably in a combined form to facilitate patient compliance. When not in combined form, they can be administered concurrently or sequentially. For example, at least two of TAG, and the stilbene/stilbenoid component, can be administered concurrently or sequentially. For oral forms of drug delivery, tablets and capsules are preferred with the tablet form especially preferred. For example, a preferred oral daily dose range can include from about 0.1 g to about 20 g of TAG, preferably about 1 g to about 15 g of TAG, and in one exemplary embodiment, from about 2 g to 10 g of TAG particularly when used in combination with a stilbene or stilbenoid component.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

Any suitable route of administration may be employed for providing the patient with an effective dosage of the compositions according to the methods of the present invention. For example, oral, rectal, parenteral, intravenous, topical, transdermal, subcutaneous, intramuscular, and like forms of administration may be employed. Oral, topical, transdermal, or locally by inhalation dosage forms are preferred. Non-limiting exemplary dosage forms include tablets, troches, dispersions, suspensions, solutions, capsules, patches, and the like. A preferred dosage form includes tablets, in one embodiment, preferably directly compressed tablets.

The compositions for use in the methods of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets. Because of their ease of administration, tablets and capsules represent the most advantageous oral dosage unit form, in which case solid pharmaceutical carriers are employed. If desired, tablets may be coated by standard aqueous or nonaqueous techniques. For example, a tablet may be prepared by direct compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound optionally moistened with an inert liquid diluent. Desirably, each tablet contains a single dose of the pharmaceutical composition(s) as discussed herein.

In one embodiment, the second active drug component can be formed as an immediate release formulation and may be incorporated into a single dosage form with the TAG dosage, for example without limitation, by coating onto the membrane by conventional methods. In general, the second active drug component may be incorporated or combined by any pharmaceutically acceptable method into a single dosage form with the first active drug. The combination of the TAG and second active drug component and any optional prophylactic or therapeutic agent and pharmaceutically acceptable carrier, as selected, may be performed by, but is not limited to, processes such as drug layering, coating, lamination, dry compression, deposition and printing. The TAG, second active component (e.g., a combination of D-tagatose and a stilbene or stilbenoid component), or both, can be prepared in controlled or sustained release form, for example without limitation, in association with a gel, matrix, capsule, or resin material, or any combination of controlled release, sustained release, or delivery device technology available to those of ordinary skill in the art as an alternative or in addition to the common dosage forms set out above, such as those described in, for example without limitation, U.S. Pat. Nos. 3,845,770;

3,916,899; 3,536,809; 3,598,123; and 4,008,719, et seq., the disclosures of which are each hereby incorporated herein by express reference thereto.

Pharmaceutical compositions for use in the methods of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with a pharmaceutically carrier. It should be understood that the pharmaceutical compositions of the invention can be entirely free of additional pharmaceutically acceptable carriers, given that the TAG itself can function as a diluent permitting tabletting without any additional carrier. In general, if a carrier is used, the compositions are prepared by uniformly and intimately admixing the active ingredient(s) with liquid carriers or finely divided solid carriers or both, and then, if necessary, shaping the product into the desired presentation. Various diluents, excipients, lubricants, dyes, pigments, dispersants, etc., disclosed, e.g., in Remington's Pharmaceutical Sciences (1995), may be used to optimize any component, layer, portion, or the compositions described herein as a whole based on the guidance provided herein to those of ordinary skill in the art.

Preferably, the components of a solid composition according to the invention are blended and compressed directly from a powder mixture without need for pretreatment of the powder blend by wet or dry granulation procedure. Substantially all the components preferably have a substantially or entirely uniform particle size and preferably are substantially free or entirely free of air entrapped in the tablets during direct compression. Indeed, it is preferred that the composition(s) of the present invention be at least substantially free, preferably entirely free, of large particulates or other impurities. Due to the nature and physical properties of TAG, in one embodiment it is preferred that no binders or other cohesive substances be used during direct compression of the tablets. The exemplary tablets may be manufactured by other granulation procedures that are available in the art. Additionally, other excipients such as lubricants, pigments or dyes may also be employed in the formulation of the subject invention. Alternatively, the components may be dissolved into a liquid solution that is to be taken orally or by intramuscular, subcutaneous, or intradermal injection. When the compounds of the present invention are formulated into oral preparations, an excipient, a binder, a disintegrant, a lubricant, a colorant, a corrigent and the like can be added thereto as required, and the resulting mixture is formed into tablets, coated tablets, granules, capsules or the like. When preparing injections, a pH adjustor, a buffer, a stabilizer, an antiseptic and the like can be added. Injections can be made in a conventional manner as known to those of ordinary skill in the art. Due to the comparatively low absorption rate of TAG when taken orally, adjustment to dosage amount would be necessary if injected into the bloodstream.

The active drug components of the pharmaceutical compositions, including any form of TAG or a stilbene or stilbenoid component, can be obtained by any chemical isolation, chemical synthesis or a combination thereof available to those of ordinary skill in the art. Preferably, the components of the pharmaceutical composition are at least substantially pure, and more preferably are pure with no more than trace amounts of impurities. Any suitable purification techniques can be carried out in association with the compositions of the invention using suitable processes generally available to those of ordinary in the art, such as, but not limited to, filtration, extraction, distillation, fractionation, and crystallization. Preferably, the components of the pharmaceutical composition are at least substantially or essentially free of, preferably are entirely free of, detectable amounts of other material that normally accompany the material as it is found in its native state. Moreover, for human administration, preparations should meet sterility, pyrogenicity, and the general safety and purity standards as required by FDA Office of Biologics standards.

The phrase "pharmaceutically" in connection with the effective amount includes that amount of D-tagatose, alone or in combination with other active ingredient(s), that either acts as a prophylactic and inhibits or prevents the development of and/or provides a prophylactic or therapeutic benefit in the treatment or management of symptoms or conditions associated with the treatment of the metabolic syndrome, atherosclerosis, obesity or diabetes, or a combination thereof, including, but not limited to, the symptoms thereof. Such symptoms include, without limitation, hypertension, high glycated hemoglobin levels in the blood, high blood pressure, dyslipoproteinemia, hypertriglyceridemia, high C-reactive protein concentrations in the blood, or high concentrations of LDLs as well as low concentrations of high density lipoproteins HDLs, or one or more other conditions or symptoms associated therewith.

For example, in one embodiment of the invention the pharmaceutical compositions described herein are administered in an amount sufficient to lower or decrease the total serum triglyceride levels by about 1% to about 60%, preferably about 5% to about 50%, more preferably about 11% to about 40%. Lowering serum triglyceride levels can be an important aspect of reducing the risk or severity of the metabolic syndrome, atherosclerosis, obesity or diabetes in a mammal, particularly a human. In another embodiment, the pharmaceutical compositions described herein are administered in an amount sufficient to lower or decrease the concentration of LDL in the blood by about 0.1% to about 30%, preferably about 4% to about 20%, more preferably about 6% to about 10%. Lowering LDL concentrations in the blood can also be advantageous in reducing the risk or severity of the metabolic syndrome, atherosclerosis, obesity or diabetes in a mammal, particularly a human.

In another embodiment, the pharmaceutical compositions described herein are administered in an amount sufficient to lower or decrease the plaque volume in arteries by about 0.1% to about 50%, preferably about 0.5% to about 40%, more preferably about 1% to about 30%. For the purposes of this invention, "plaque" includes any deposit on, or thickening of, the arterial lining exceeding about 0.5 mm. Lowering the plaque volume in arteries is an important aspect of reducing the risk or severity of the metabolic syndrome, atherosclerosis, obesity or diabetes in a mammal, particularly a human.

The present invention also provides methods of treating symptoms or conditions associated with the metabolic syndrome, atherosclerosis, obesity or diabetes mellitus, or a combination thereof, including the symptoms of hypertension, high glycated hemoglobin levels in the blood, high blood pressure, dyslipoproteinemia, hypertriglyceridemia, high C-reactive protein concentrations in the blood, or high concentrations of LDLs as well as low concentrations of high density lipoproteins HDLs, or one or more other conditions or symptoms associated therewith, for example, preferably in a mammal, more preferably in a human. The methods of the invention include administering to a patient, preferably a mammal, more preferably a human, an effective amount of a TAG composition of the invention.

The effective amount of the composition will vary depending on the subject being treated, the severity of the disease state and the manner of administration, and may be determined routinely by one of ordinary skill in the art. The dose, and perhaps dose frequency, will also vary according to the age, body weight, and response of the individual. In an exemplary composition, a pharmaceutically effective amount of TAG in an oral tablet form is a concentration of about 2.5 grams, wherein the tablet is administered from about one to about three times daily, such as with meals. In other exemplary compositions where the dosage form is, e.g., divided in three daily doses, the pharmaceutically effective amount of D-tagatose can include amounts of about 0.67 grams, about 0.83 grams, about 1.67 grams, about 5 grams, about 7.5 grams, about 8.3 grains, about 10 grams, about 12.5 grams, about 15 grams and about 16.67 grams per dose. In yet other exemplary compositions, the pharmaceutically effective amount of TAG can be co-administered with a pharmaceutically effective amount of at least a second active drug. Typically, for the resveratrol or resveratrol derivative component, dosing of about 0.05 to about 50 mg per kg of body weight may be preferred, with dosing of about 0.1 to about 10 mg per kg of body weight especially preferred, although there can be significant dosing variation outside of this range to achieve the desired therapeutic or prophylactic effect according to the invention, which may depend on the amount of TAG present in the composition. It may be necessary to use dosages outside the above ranges in some cases, as will be apparent to those of ordinary skill in the art. Further, it is noted that the clinician or treating physician will know the appropriate daily dose, and how and when to interrupt, adjust, or terminate therapy in conjunction with individual patient response.

In one embodiment, the invention relates to a method of treating the metabolic syndrome in a mammal by administering to the mammal a prophylactically or therapeutically effective amount of a composition of TAG. In another embodiment, the invention relates to a method of treating atherosclerosis in a mammal by administering to the mammal a prophylactically or therapeutically effective amount of a composition of TAG. In these embodiments, it is preferred that TAG is the sole active ingredient in the composition. In another embodiment, the invention relates to a method of preventing the metabolic syndrome in a mammal by administering to the mammal a prophylactically effective amount of a composition of TAG. In another embodiment, the invention relates to a method of preventing atherosclerosis in a mammal by administering to the mammal a prophylactically effective amount of a composition of TAG. In these embodiments, it is preferred that TAG is the sole active ingredient in the composition.

In other embodiments, the methods administer pharmaceutically effective compositions including TAG compositions along with a second pharmaceutical drug component to provide an additive, more complete, or synergistic effect in preventing, treating, or managing a condition or disease, or its symptoms, as discussed herein, or any other disease or condition for which the same patient may require prevention, treatment, or management thereof. In various embodiments, an unexpected, beneficial synergistic effect may occur as a result of the application of a combination of TAG and a second active drug component, such as the stilbene or stilbenoid component, in the pharmaceutical compositions discussed herein. As a result, a lower dose of the second active drug component in combination with the TAG component can be used to achieve the effect expected by a significantly larger dose of the second active drug component alone. Conversely, in some embodiments, a lower dose of TAG can be used in combination with a second active drug to achieve the effect expected by a significantly larger dose of the TAG alone. For example, preparations of pharmaceutical compositions herein could render a 0.075 g dose of stilbene or stilbenoid component in combination with an effective amount of TAG more effective in preventing, treating or managing a condition or disease discussed herein, or its symptoms, compared to a 0.15 g or greater dose of stilbene or stilbenoid component alone that is at least substantially or entirely free of TAG. For instance, the presently described pharmaceutical compositions may be administered to prevent, treat, or manage obesity; diabetes; atherosclerosis; the metabolic syndrome; or one or more conditions associated with the symptoms or disease state of the metabolic syndrome; any symptom(s) thereof; or a combination of any of the foregoing diseases, symptoms, or conditions. In one exemplary embodiment, a method of preventing, treating, or managing a disease in a mammal includes administering to the patient a pharmaceutically effective amount of an oral tablet including a composition of a pharmaceutically effective amount of TAG and stilbene/stilbenoid component.

The compositions of the present invention can be administered in connection with combination therapy regimens, e.g., for preventing, treating, or managing the symptoms of the metabolic syndrome, atherosclerosis, obesity, or diabetes, or a combination thereof. For those embodiments of the invention where the composition is administered with another agent effective for treating the symptoms of the metabolic syndrome, for example, and depending on the needs of the individual patient as determined by a clinician or treating physician, such additional prophylactic or therapeutic agents may include, for instance, one or more effective agents such as diuretics, ACE inhibitors and cholesterol-lowering drugs or any combination thereof.

The compositions may also include one or more other classes of pharmaceutically active agents for the prevention, treatment, or management of other conditions, as deemed necessary or desired by a physician. Such other conditions may occur, for example, in patients that are also suffering from one or more related conditions. Other conditions may include, but are not limited to, for example, gout, polycystic ovarian syndrome and endothelial dysfunction. In one embodiment, the invention provides for a composition for use in preventing, treating or ameliorating the symptoms of the metabolic syndrome in a mammal. In another embodiment, the invention provides for a composition for use in preventing, treating or ameliorating the symptoms of atherosclerosis in a mammal. In yet another embodiment, the invention provides for a composition for use in preventing, treating or ameliorating the symptoms of obesity in a mammal. In another embodiment, the invention provides for a composition for use in preventing, treating or ameliorating the symptoms of diabetes in a mammal. In some embodiments, an advantage may be achieved by formulating the composition to include at least two active drugs, one of which is TAG, each present in the composition is an amount effective to treat, prevent or lessen the symptoms of the metabolic syndrome, in the individual.

The invention also provides for the use of TAG-based compounds in the manufacture of one or more medicaments for treating, preventing, or ameliorating one or more clinical symptoms of the metabolic syndrome in general as well as atherosclerosis, obesity and diabetes. Such compositions may also include one or more pharmaceutically acceptable carriers useful in the preparation of medicaments suitable for systemic or local administration to a mammal having, suspected of having, or at risk for developing the metabolic syndrome, as well as atherosclerosis, obesity and diabetes.

In another embodiment, the invention provides for the use of TAG-based compounds in the manufacture of one or more medicaments for treating, preventing, or ameliorating one or more clinical symptoms of the metabolic syndrome in general as well as atherosclerosis, obesity and diabetes. Use of a composition including at least TAG and a second active drug, preferably a stilbene or a stilbenoid component, or any pharmaceutically acceptable salt, alcohol, hydrate, ester, amide, derivative, analog, polymorph, metabolite, isomer, or prodrug form thereof, or any combination thereof, formulated for administration to the mammal in the manufacture of a medicament for preventing, treating or ameliorating the symptoms of the metabolic syndrome, atherosclerosis, obesity, diabetes, or a combination thereof, are also provided herein.

In another embodiment, the present invention discloses composition and methods for the prevention, treatment, amelioration of symptoms of the metabolic syndrome, atherosclerosis, obesity, and diabetes including, but not limited to hypertension, hypertriglyceridemia, hyperglycemia, hypercholesterolemia, or a combination thereof.

The compositions disclosed herein, and compositions that include, consist essentially of, or consist of them, have been shown to be effective in lowering LDL, serum triglyceride, HbA1c levels, as well as the number of atherosclerotic lesions present in susceptible individuals, and can thus be used as either as a monotherapy, or alternatively in combination with one or more known prophylactic or therapeutic agent(s) to provide regimen(s) that cure or significantly diminish the dynamics of the development of the metabolic syndrome, atherosclerosis, obesity or diabetes in vivo. The determination of individual dose size, duration of therapy, the need for concomitant co-therapy using additional compounds, as well as all other dosing considerations is considered to be well within the purview of the ordinary skilled medical practitioner carrying out the methods of the invention.

The invention is also particularly contemplated to be useful in persons who are placed at a higher risk for developing the metabolic syndrome, atherosclerosis, obesity and diabetes, such as those individuals currently with hypertension, hypertriglyceridemia, hyperglycemia, hypercholesterolemia, or a combination thereof.

In another embodiment, the present invention relates to a food product including a first active ingredient, preferably TAG, in combination with at least one second active ingredient. It should be understood that the term "food product" includes anything edible by a mammal, including liquid, that has nutritional content, such as without limitation, a fortified food supplemented with the composition of the invention, a nutritional supplement including the composition of the invention, or the like. The second active ingredient may be any drug or prodrug useful in combination therapy with TAG. In one embodiment, the preferred second active drug is a stilbene, stilbenoid, their pharmaceutically acceptable salts, alcohol, hydrate, ester, amide, derivative, analog, polymorph, metabolite, isomer, or prodrug forms forms. These compounds may be obtained by chemical synthesis or from plants. The stilbene compounds of the present invention can be formed as described above. Preferred stilbenes and stilbenoids include piceatannol, pinosylvin, pterostilbene, resveratrol, viniferins, ampelopsin A, ampelopsin E, diptoindonesin C, diptoindonesin F, gnetin H, hemsleyanol D, hopeaphenol, trans-diptoindonesin B, vaticanol B, astringin, piceids, and diptoindonesin A. A preferred stilbenoid for use in the present invention is resveratrol and/or its derivatives.

Especially preferred resveratrol-derived components of the second active drug include resveratrol dimers, more preferably resveratrol trans-dehydrodimer, resveratrol (E)-dehydrodimer 11'-O-β-D-glucopyranoside, resveratrol (E)-dehydrodimer 11-O-β-D-glucopyranoside and viniferins, or isomers thereof. Both ingredients (e.g., TAG and a stilbene or stilbenoid component) may be incorporated into any food product by any means known to those of ordinary skill in the art.

In one embodiment, the compositions or food products are at least substantially free, or entirely free, of any sweetener or bulking agents aside from the TAG and possibly the second active drug component. Exemplary sweeteners and bulking agents that could be included, but in one embodiment are minimized or avoided, include without limitation: neotame, sucralose, saccharin, acesulfame potassium, aspartame, fructose, invert sugar, high fructose corn syrup, sucrose, xylitol, maltitol, glucose, sorbitol, mannitol, maltose, trehalose, regular corn syrup and/or lactose.

The term "about," as used herein, should generally be understood to refer to both numbers in a range of numerals even if it appears only before the first number in a range. Moreover, all numerical ranges herein should be understood to include each whole integer and tenth of an integer within the range.

The terms "active agent," "active ingredient," and "drug" in some cases with the term "component" are used interchangeably herein to refer to one or more chemical materials or compounds which, when administered to a mammal, induce(s) a desired pharmacological, prophylactic, or therapeutic effect. Included are any pharmaceutically acceptable salt, alcohol, hydrate, ester, amide, derivative, analog, polymorph, metabolite, isomer, or prodrug forms, of those compounds or classes of compounds, particularly those specifically mentioned, that also induce the desired pharmacological, prophylactic, or therapeutic effect.

The term "amount" includes both a dry quantity of an agent, compound, or component, such as a quantity that is measured or given in gram (g) units, as well as a quantity of an agent, compound, or component that is dissolved or otherwise present in a particular volume of a solvent or other liquid reagent and expressed in terms of a concentration, such as mg/dl. The term "effective amount" or "pharmaceutically effective amount" includes an amount of an active pharmaceutical agent that is required to obtain prophylactic or therapeutic efficacy against a disease or condition, or a symptom thereof, or to manage a disease or condition, or a symptom thereof. The exact amount required will vary from subject to subject, depending on the age, weight, and general condition of the subject, the severity of the condition being treated, the judgment of the clinician, and the like. Thus, it is not always possible to specify an exact "effective amount." An appropriate "effective" amount in any individual case, however, may be determined by one of ordinary skill in the art using only routine experimentation. For instance, an "effective amount" or "pharmaceutically effective amount" of any portion of the compositions described herein, as well as each entire composition, are encompassed by the frequency and dosage amounts described herein. By way of example, an effective amount of TAG includes an amount of TAG, or a salt, sugar alcohol, hydrate, solvate, ester, amide, derivative, analog, metabolite, prodrug thereof, that is required to obtain efficacy to prevent, treat, or manage the metabolic syndrome condition, or the formation or retention thereof, or the symptoms or conditions associated with the metabolic syndrome condition. The term "manage" includes any action that results, for instance, in the amelioration of a disease or condition, or other therapeutic effect that improves the health or well-being of a patient such as the prevention or reduction of its symptoms without necessarily completely curing the disease or condition.

As used herein, the terms "comprise," "comprises," and "comprising" and "include," "includes," and "including" encompass other transition terms including, but not limited to, "consists of," "consisting of," "consists essentially of," and "consisting essentially of." As such, each embodiment according to the invention should be understood as alternatively being described with reference to each of these other transition terms even though these other terms are noted only in this paragraph to minimize the need for repetitive language throughout the application.

As used herein, "mammal" is meant the class of warm-blooded vertebrate animals that have, in the female, milk-secreting organs for feeding the young. Mammals include, without limitation, humans; apes; various four-legged animals such as cows, horses, pets such as dogs and cats; whales; dolphins; and bats.

The term "pharmaceutically acceptable salt(s)" or "a pharmaceutically acceptable salt thereof" refers to salt(s) prepared from pharmaceutically acceptable non-toxic acid or bases including inorganic acids and bases and organic acids or bases. The pharmaceutically acceptable salts used in the present invention may be amphoteric, may be present in the form of internal salts, or both. Although any available salt made by any method available to those of ordinary skill in the art may be used, a few exemplary acids and bases are described without limitation. Exemplary inorganic acids that can be used to form such salts include one Or more mineral acids such as hydrochloric, hydroiodic, hydrobromic, sulfuric or phosphoric acid. Appropriate organic acids may be selected, for example without limitation, from aliphatic, aromatic, carboxylic and sulfonic classes of organic acids, examples of which are formic acid, acetic acid, propionic acid, succinic acid, glycolic acid, glucuronic acid, furoic acid, benzoic acid, anthranilic acid, salicylic acid, phenylacetic acid, mandelic acid, embonic (pamoic) acid, methanesulfonic acid, ethanesulfonic acid, pantothenic acid, benzenesulfonic acid, stearic acid, sulfanilic acid, algenic acid, galacturonic acid, oxalic acid, fumaric acid, maleic acid, mac acid, citric acid, tartaric acid, glutamic acid, or a combination thereof. Examples of such inorganic bases, for potential salt formation with sulfate or phosphate compounds of the invention, include metallic salts made from aluminum, sodium, potassium, lithium, ammonium, calcium, magnesium, and zinc salts, and any combination thereof. Salts derived from organic bases include, for example, one or more salts of primary, secondary and tertiary amines, substituted amines including naturally-occurring substituted amines, and cyclic amines, including isopropylamine, trimethylamine, diethylamine, tripropylamine, ethanolamine, 2-dimethyl aminoethanol, trimethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, fumarate, maleate, succinate, acetate, N,N-dibenzylethylenediamine, chloroprocaine, choline, diethanolamine, ethylenediamine, meglumaine (N-methylglucamine), and oxalate.

As used herein, the term "prevent," "preventing" or "prevention" covers preventing the specified disease and/or its symptoms in a mammal, more preferably a human, and includes: (i) preventing the disease or its symptoms from occurring in a subject that may be predisposed to the disease but has not yet been diagnosed as having it; and (ii) inhibiting the disease or its symptoms, i.e., arresting its development before or after it afflicts a patient, or both. It should be understood that symptoms of any disease are also encompassed within the terms "prevent," "preventing" or "prevention" such that inhibiting symptoms of the metabolic syndrome, for example, may address some or all of the symptoms thereof with or without actually affecting the underlying disease itself.

The term "substantially" means, e.g., not entirely complete, or not entirely absolute. Typically, "substantially" should be understood to refer to at least about 90 percent, preferably at least about 95 percent, and more preferably at least about 99 percent. In one more preferred embodiment, "substantially" can refer to at least about 99.5 percent or 99.9 percent. In one example, a composition that is "substantially stable," such as a formulation of TAG having substantial stability, encompasses a solution that may not necessarily exhibit absolute or 100% stability over a defined period of time; instead, the composition may exhibit nearly total stability, such as greater than about 97% stability or 99.8% stability, over a particular period of time under ambient conditions (unless specified otherwise).

Conversely, "substantially free" means, e.g., almost entirely devoid of the referenced characteristic. Typically, "substantially free" should be understood to refer to less than about 5 percent, preferably less than about 1 percent, and more preferably less than about 0.1 percent. In a more preferred embodiment, it refers to less than about 0.05 percent, or less than about 0.01 percent. In one most preferred embodiment, the term refers to less than an analytically detectable amount.

As used herein, the term "treat," "treating" or "treatment" covers treating or managing the specified disease and/or its symptoms in a mammal, more preferably a human, and includes: (i) relieving the disease or its symptoms, i.e., causing regression of the disease; (ii) monitoring the disease or its symptoms, i.e., adjustment of the drug delivery cycle to optimum levels. It should also be understood that symptoms of any disease are also encompassed within the terms "treat," "treating," or "treatment" such that managing symptoms of the metabolic syndrome, for example, may address some or all of the symptoms thereof with or without actually affecting the underlying disease itself.

Each of the patent applications, patents, publications, and other published documents mentioned or referred to in the Detailed Description is incorporated herein in its entirety by express reference thereto, to the same extent as if each was specifically and individually indicated to be incorporated by reference.

EXAMPLES

The invention is further defined by reference to the following illustrative (non-limiting) examples, describing in detail specific excipients, indications, combinations, dosage amounts, and the like, that may be used to help one of ordinary skill in the art prepare or administer the compositions and carry out the methods of the present invention.

Example 1

Comparison of Body Weight, Adipocyte Characteristics, Blood Cholesterol Concentrations, Hyperglycemia, and Atherosclerotic Lesions in Control, TAG-Fed and Sucrose-Fed Hypercholesterolemic Mice According to the Invention Low-density lipoprotein receptor male and female mice (LDLr$^{-/-}$) that were approximately eight weeks old were fed either a standard murine diet ("control"), a diet enriched with sucrose, or a diet enriched with TAG for sixteen weeks. The diets enriched with sucrose or TAG contained equivalents amounts (g/kg) of protein, fat and carbohydrate, although due to the differences in energy content between sucrose (~4.0 kcal/g) and TAG (~1.5 kcal/g), the TAG-containing diet provided relatively more calories from fat and protein. Before the sixteen week feeding period, sucrose and TAG were introduced to the experimental mice gradually over a three week period, using an increasing ratio of sucrose or TAG diet to the standard murine diet.

Food intake was measured for the first four weeks of the sixteen week period and the body weight of the mice was measured weekly. In both genders, mice fed a diet enriched with sucrose exhibited a marked increase in body weight (40±2 g for males; 31±1 g for females) compared to the mice fed a diet enriched with TAG (27±0 g for males; 24±1 g for females) and the control (30±0 g for males; 24±1 g for females) mice. The body weights of mice fed a TAG enriched diet were comparable to the body weights of the control mice. At the study end point, retroperitoneal and epidydimal fat was dissected out of the body and stored in formalin and subsequently embedded in paraffin for examination of morphology and immunostaining. Total adipose tissue mass was increased in both male and female mice fed the diet enriched with sucrose when compared to mice fed murine or TAG-enriched diets. For characterization of adipocyte morphology, adipose tissue sections were deparraffinized and stained using hematoxylin and eosin and then analyzed using Image Pro Plus 5.1 (Media Cybernetics, Silver Spring, Md.). Mice fed the sucrose-enriched diet exhibited increased adipocyte size (83±3 µm for males; 50±1 µm for females) when compared to TAG-fed (79±3 µm for males; 31±1 µm for females) and control (74±3 µm for males; 30±1 µm for females) mice. Macrophage positive F4/80 immunostaining was detected in adipose section from mice fed a sucrose-enriched diet but not in those fed standard murine or TAG-enriched diets. Results from this study indicate that a sucrose-enriched diet promotes the development of obesity, while TAG surprisingly did not promote substantial weight gain, enhanced adiposity or adipocyte hypertrophy.

Total serum cholesterol and plasma triglyceride concentrations were determined for the individual mice at the end of the study using enzymatic assay kits (Wako Pure Chemical, Richmond, Va.). Male and female mice fed sucrose-enriched diets had markedly increased total serum triglyceride (822±148 mg/dl for males; 326±37 mg/dl for females) concentrations compared to male and female mice fed standard murine (110±20 mg/dl for males; 79±16 mg/dl for females) and TAG (162±29 mg/dl for males; 54±8 mg/dl for females) diets. Male and female mice fed sucrose-enriched diets had markedly increased total serum cholesterol concentrations compared to male and female mice fed standard murine and TAG diets. In addition, male and female mice fed sucrose-enriched diets had significantly elevated concentrations of very low density lipoprotein and LDL cholesterol. In comparison, male and female mice fed TAG-enriched diets had only slightly elevated concentrations of very low density lipoprotein and LDL cholesterol compared to male and female control mice. Total serum cholesterol levels were surprisingly and unexpectedly decreased in both male and female TAG-fed mice as compared to sucrose-fed mice.

At the study end point, mice were exsanguinated by perfusion through the left ventricle. Aortic tissues from the heart to the ileal bifurcation were dissected and fixed overnight in 4% paraformaldehyde made with phosphate buffered solution ("PBS") and then stored in PBS. Atherosclerosis was quantified by en face analysis of lesion surface area as detailed in Henriques, T A, et al., "Orchidectomy, but not ovariectomy, regulates angiotensin II-induced vascular diseases in apolipoprotein E-deficient mice," *Endocrinology*, 145: 3866-3872 (2004). Atherosclerotic lesions were quantified by two independent observers. There was a striking increase in atherosclerotic surface area in male and female mice fed a sucrose-enriched diet compared to both control and mice fed a TAG-enriched diet. TAG-fed male mice did not exhibit a significantly different amount of atherosclerosis compared to control mice but female mice did exhibit a slightly higher rate of atherosclerosis than control mice. Macrophage infiltration into atherosclerotic areas was assessed using immunohistochemistry staining. Sucrose-fed mice exhibited a larger degree of macrophage infiltration and larger lesions in aortic roots when compared to TAG-fed mice. Infrared microscopy was then performed on the aortic lesions and atherosclerotic lesions of the sucrose-fed mice had the highest concentration of lipids compared to the lesions in TAG-fed and control mice. TAG-fed mice had an intermediate amount of lipids but Gomori Trichome staining of the lesions revealed that there was a higher concentration of collagen in the atherosclerotic lesions of the TAG-fed mice compared to the lesions in the sucrose-fed mice. Collagen may strengthen the fibrous caps in lipid-filled atheromas, preventing rupture. Thus, both male and female sucrose-fed mice exhibited a surprisingly greater number and size of atherosclerotic lesions in aortic roots when compared to TAG-fed mice.

Example 2

Serum Triglyceride and Cholesterol Level Variance with TAG Dosage According to the Invention Thirty-eight human patients with type 2 diabetes were administered one of three concentrations of TAG orally with meals. The three different doses were 2.5, 5.0, and 7.5 g. The treatment duration was six months and patients were randomized to one of the three doses. Patients were required to pass specific inclusion criteria including HbA1c, or glycated hemoglobin, levels between 6.6% and 9.0%. Patients also had to go through an eight week run-in period in which they were on a weight-maintaining diet and a daily exercise program under the supervision of the investigator prior to receiving their TAG dose. Patients with a current or recent history of treatment with any oral or injectable anti-diabetic treatment, as well as patients having one or more episodes of severe hypoglycemia within six months prior to entry into the study, were excluded from the study. Blood samples were taken throughout the experiment and levels of HbA1c, serum triglycerides, LDLs and HDLs were measured.

After six months on TAG, the patients in the 7.5 g group experienced an average reduction of 0.3% in HbA1c from the HbA1c of the 2.5 g group. The 5 g group experienced an average reduction of 0.05% in HbA1c from the HbA1c of the 2.5 g group.

TAG also surprisingly decreased the average serum triglycerides of the TAG-consuming patients by about 59 mg/dl by the end of the first month on the therapy, a decrease from baseline that remained at about 41 mg/dl by the end of the six months of the experiment. After the six months on TAG, the patients in the 2.5 g group surprisingly experienced an average reduction of 22.2 mg/dl, the patients in the 5 g group surprisingly experienced an average reduction of 96.8 mg/dl and the patients in the 7.5 g group surprisingly experienced an average reduction of 2.8 mg/dl.

TAG also decreased the serum LDL by an average of about 13 mg/dl by the end of the first month on the therapy, while serum HDL was essentially unchanged. LDL levels in patients in the 2.5 g group surprisingly decreased by about 12.3 mg/dl and in the 5 g group surprisingly by about 23.8 mg/dl by the end of the first month of therapy. The LDL:HDL ratio was unexpectedly improved for two of the three dose groups (i.e., the 2.5 g and 5 g groups) by an average of 0.3.

Example 3

TAG Tablet Formation According to the Invention

The formation of a TAG composition tablet by direct compression is exemplified by the following, although different second active drug compositions can be used.

TAG is passed through a 40 mesh stainless steel screen and blended with resveratrol trans-dehydrodimer granules for approximately five (5) minutes. After blending, the granules are compressed on a rotary press fitted with 15/32" round standard concave punches (plain lower punch, upper punch with an approximately 1 mm indentation pin). The orifice may be formed by any means commonly employed in the pharmaceutical industry.

Although preferred embodiments of the invention have been described in the foregoing description, it will be understood that the invention is not limited to the specific embodiments disclosed herein but is capable of numerous modifications by one of ordinary skill in the art. It will be understood that the materials used and the chemical or pharmaceutical details may be slightly different or modified from the descriptions herein without departing from the methods and compositions disclosed and taught by the present invention, and that such modifications are also intended to fall within the scope of the appended claims. The foregoing disclosure includes all the information deemed essential to enable those of ordinary skill in the art to practice the claimed invention.

What is claimed is:

1. A method for decreasing a level of a triglyceride, a low-density lipoprotein, or a cholesterol in a subject in need thereof, the method comprising: administering a composition comprising a pharmaceutically effective amount of a first pharmaceutically active drug which comprises D-tagatose, or a pharmaceutically acceptable salt, sugar alcohol, hydrate, solvate, ester, amide, or prodrug thereof, and a pharmaceutically effective amount of a second pharmaceutically active drug which comprises a stilbene or stilbenoid component or any pharmaceutically acceptable salt, alcohol, hydrate, ester, amide, polymorph, isomer, or prodrug or combination thereof, thereby decreasing the level of said triglyceride, said low-density lipoprotein, or said cholesterol in said subject.

2. The method of claim 1, wherein the second pharmaceutically active drug comprises a stilbene or stilbenoid component, or any pharmaceutically acceptable salt thereof.

3. The method of claim 2, wherein the stilbene or stilbenoid component comprises resveratrol or a resveratrol derivative, or a combination thereof.

4. The method of claim 3, wherein the resveratrol derivative comprises a resveratrol dimer.

5. The method of claim 4, wherein the resveratrol dimer comprises resveratrol trans-dehydrodimer, resveratrol (E)-dehydrodimer 11'-O-β-D-glucopyranoside, resveratrol (E)-dehydrodimer 11-O-β-D-glucopyranoside and viniferins, or an isomer thereof, or a combination thereof.

6. The method of claim 1, wherein the composition is effective to decrease a total serum triglyceride level in a patient's blood by about 1% to about 60%.

7. The method of claim 1, wherein the composition is effective to decrease a concentration of low-density lipoprotein in a patient's blood by about 0.1% to about 30%.

8. The method of claim 1, wherein the composition is effective amount to decrease plaque volume in a patient's arteries by about 0.1% to about 50%.

9. The method of claim 3, wherein the resveratrol derivative comprises trans-pieced.

10. The method of claim 1, wherein the amount of D-tagatose in the composition is effective to treat a disease associated with an abnormally increased level of a total serum triglyceride, a low-density lipoprotein, or a combination thereof.

11. The method of claim 10, wherein the disease is the metabolic syndrome, atherosclerosis, obesity, diabetes, or a combination thereof.

12. The method of claim 1, wherein the amount of D-tagatose in the composition is effective to reduce the severity of progression of a disease associated with an abnormally increased level of a total serum triglyceride, a low-density lipoprotein, or a combination thereof.

13. The method of claim 12, wherein the disease is the metabolic syndrome, atherosclerosis, obesity, diabetes, or a combination thereof.

* * * * *